United States Patent [19]
Amirkhanian et al.

[11] Patent Number: 5,349,590
[45] Date of Patent: Sep. 20, 1994

[54] MEDICAL LASER APPARATUS FOR DELIVERING HIGH POWER INFRARED LIGHT

[75] Inventors: Varouj D. Amirkhanian, Glendale; Colette Cozean, El Toro; Robert J. Freiberg, Mission Viejo, all of Calif.

[73] Assignee: Premier Laser Systems, Inc., Irvine, Calif.

[21] Appl. No.: 75,720

[22] Filed: Jun. 11, 1993

Related U.S. Application Data

[63] Continuation of Ser. No. 866,876, Apr. 10, 1992, abandoned.

[51] Int. Cl.⁵ .............................................. H01S 3/30
[52] U.S. Cl. ........................................ 372/6; 385/102
[58] Field of Search ............................ 372/6; 385/102

[56] References Cited

U.S. PATENT DOCUMENTS

| | | |
|---|---|---|
| 4,826,431 | 5/1989 | Fujimura et al. |
| 4,898,777 | 2/1990 | Kindler et al. |
| 4,988,163 | 1/1991 | Cohen et al. |
| 5,024,506 | 6/1991 | Hardin et al. ........... 385/102 |
| 5,045,507 | 9/1991 | Tran . |
| 5,055,120 | 10/1991 | Tran et al. |

OTHER PUBLICATIONS

Nelson, J. Stuart, MD, PhD., et al., "Ablation of Bone and Methacrylate by a Prototype Mid-Infrared Erbium: YAG Laser", *Lasers in Surgery and Medicine*, vol. 8, Jan. 1988, pp. 494–500.

Hoke, James A., DDS, MS, et al, "Erbium: YAG (2.94 μm) Laser Effects on Dental Tissues", *Journal of Laser Applications*, (Summer/Fall 1990), pp. 81–85.

*Primary Examiner*—Rodney B. Bovernick
*Assistant Examiner*—Robert E. Wise
*Attorney, Agent, or Firm*—Knobbe, Martens, Olson & Bear

[57] ABSTRACT

A medical laser apparatus which comprises a medical laser and a waveguide is used to deliver infrared energy to a treatment site. The medical laser preferably delivers electromagnetic radiation at a wavelength of about 3.0 microns such as an Er:YAG laser (wavelength of 2.94 microns). The waveguide comprises a fluoride-based guiding structure surrounding an outer protective structure, and is capable of transmitting invisible infrared light at a wavelength of about 3 microns at a power density of at least about 4 kilowatts per square centimeter. The guiding structure has a core and at least one cladding. The protective structure comprises a jacket of material, preferably polyimide, which is substantially impermeable to moisture and has a moisture resistance significantly higher than that of the guiding structure. The protective structure surrounds the guiding structure and juxtaposed therewith such that the protective structure receives a portion of the infrared light which is in the form of leaky modes and has a sufficiently high transmittance to the infrared light, such that the energy of the light in the leaky modes is dissipated from the protective structure without damaging the waveguide. The protective structure is flexible and has a relatively high resistance to bending compared to the guiding structure in order to protect the guiding structure against breakage. In one embodiment, the waveguide is used to transmit laser energy of multiple wavelengths of optical energy to a treatment site.

28 Claims, 4 Drawing Sheets

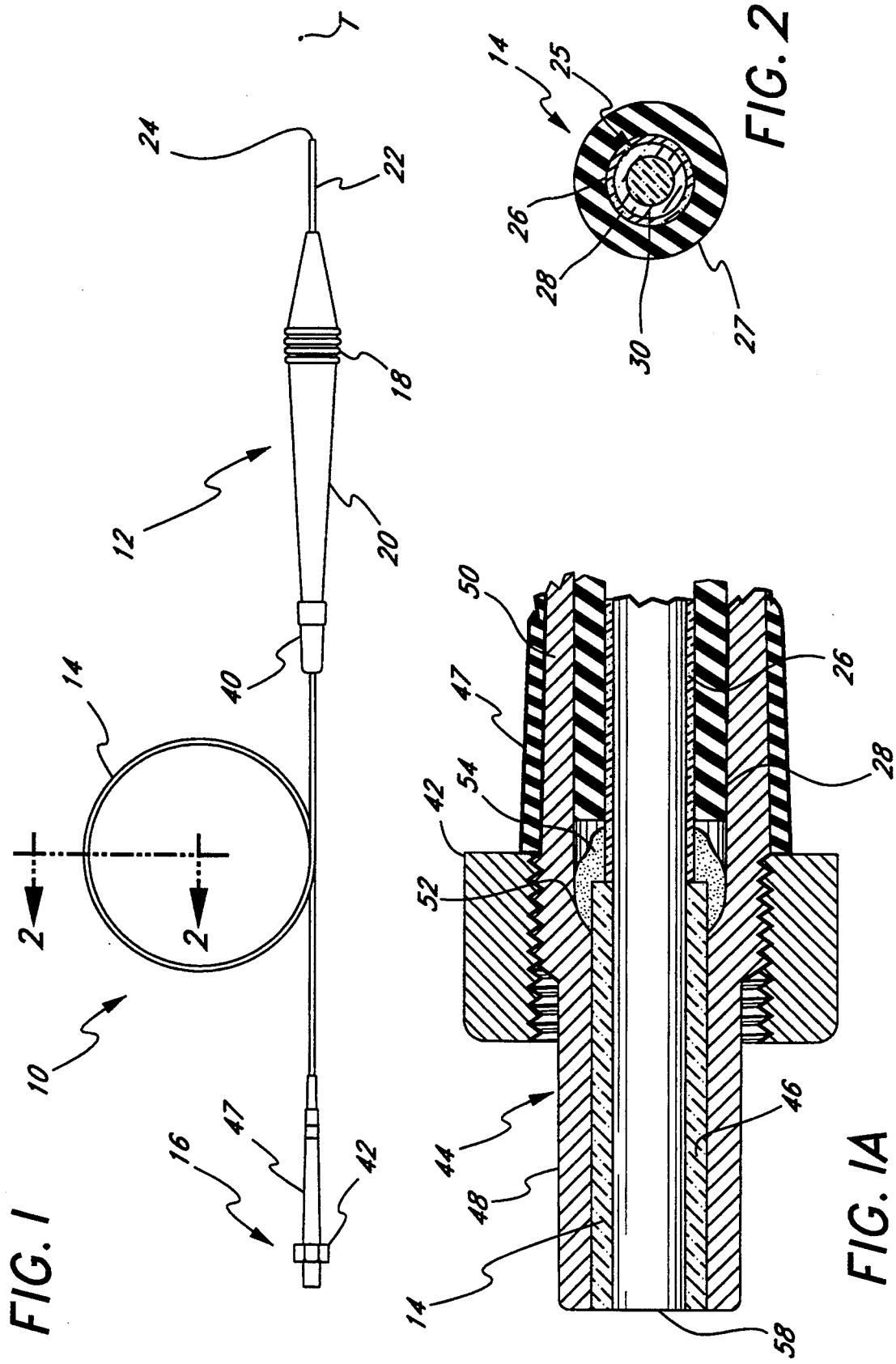

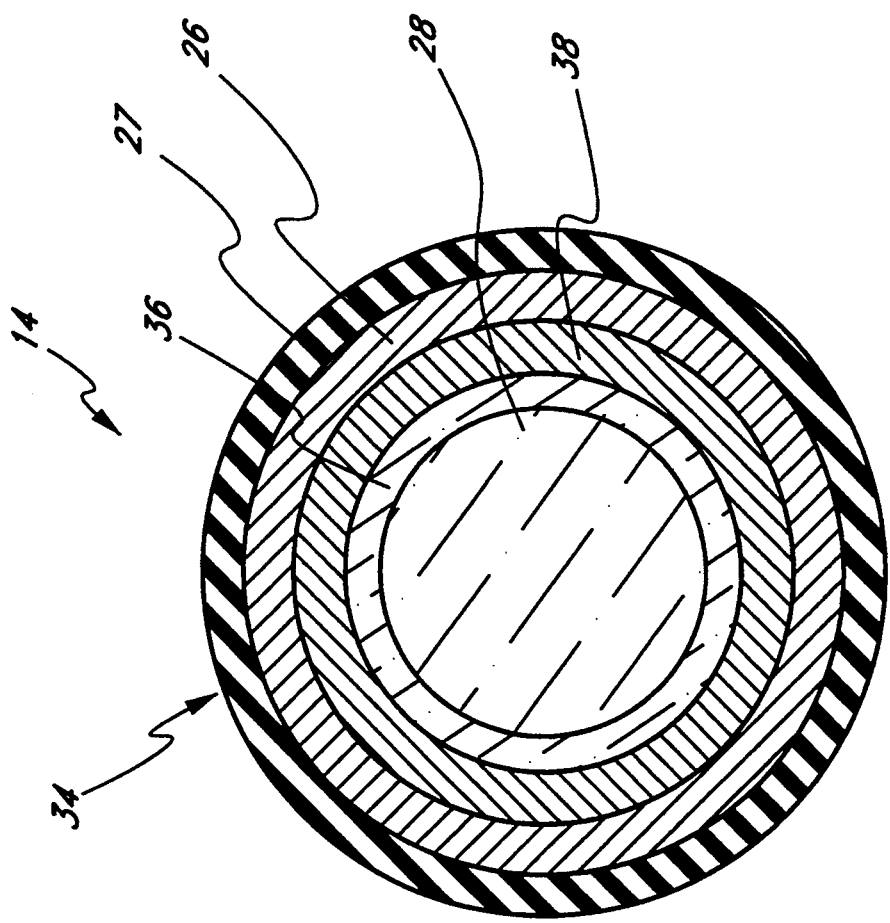

MEDICAL LASER APPARATUS FOR DELIVERING HIGH POWER INFRARED LIGHT

This application is a continuation of application Ser. No. 07/866,878, filed Apr. 10, 1992, now abandoned.

FIELD OF THE INVENTION

The present invention relates to laser energy delivery systems for laser surgery applications.

DESCRIPTION OF THE RELATED ART

It is common practice for physicians to use laser energy to perform various surgical operations. Laser light is capable of cutting, sealing, and ablating tissue, as well as coagulating blood. Erbium YAG (Er:YAG) lasers have been found to be particularly advantageous for cutting hard tissue, such as bone, and also perform well on soft tissue.

In the past, high power laser light of various different wavelengths has been transmitted to the tissue site by an articulated arm which guides the laser beam through various rigid segments of the arm. Mirrors are placed at the joints to change the beam direction. The joints are moveable, allowing the surgeon to manipulate the instrument and thereby direct the laser beam to the desired location.

An articulated arm can be very cumbersome to use, especially for high precision surgery. It is more desirable to use a fiber optic cable to direct the laser energy to the tissue site. A fiber optic cable, which directs energy by total internal reflection, allows the surgical instrument to be more readily maneuvered in any convenient direction. A cable is also lighter than a rigid instrument.

Typically, an optical fiber consists of an inner core, an outer cladding, and a buffer. The inner core transmits the laser energy. The outer cladding has a lower index of refraction than the inner core and causes the light within the inner core to be internally reflected. The different indexes of refraction are typically achieved by doping the fiber material with different impurity concentrations, a process which is well known in the art. The buffer is a layer of flexible, high strength material which is bonded to the outside of the cladding to protect the delicate core and cladding against breakage and, in the case of fluoride-based fibers, to protect the fluoride glass against moisture.

Commonly, optical fibers used to transmit certain wavelengths for medical laser surgery are composed of silica. The wavelength of Er:YAG laser light, however, tends to be absorbed by ordinary silica fiber and high power levels cannot be effectively transmitted by it. Fluoride-based fibers, on the other hand, have been shown to be good transmitters of Er:YAG laser light. Fluoride-based fibers include materials such as zirconium fluoride ($ZrF_3$), aluminum fluoride ($AlF_3$), and hafnium fluoride ($HfF_4$). These materials are also referred to as metal halides, particularly heavy metal fluorides, and they have a high transmittance in the infrared range. For the Er:YAG laser, transmission of up to 91% can be achieved through a one meter fiber at 2.94 μm.

Despite the relatively high transmittance of fluoride materials to infrared light, the power transmission capabilities of commercially available fluoride fibers are less than optimal for applications such as the aggressive cutting of human tissue, particularly hard tissue such as bone. Zirconium fluoride fibers, for example, may fail after sustained transmission of energy at very high power densities, particularly at the infrared wavelength produced by an Er:YAG laser. At such high power densities, significant amounts of laser energy escape from the core in the form of leaky modes (high order modes which are not guided within the core). The energy escaping the core travels through the cladding to the buffer, which is usually a UV acrylate. The buffer material absorbs the escaped light, and if the energy level is sufficiently high, the buffer will develop "hot spots" at which the temperature rapidly increases. The temperature of the hot spots eventually becomes high enough (higher than the fiber's glass transition temperature which is $\geq 260°$ C.) to cause the fluoride-based fiber to expand and develop microfissures or small cracks. These cracks begin to scatter the light traveling though the fiber, which creates a further build up of heat at the location of the fissures. The heat buildup rapidly causes the fiber to eventually melt or break. Thus, there is a need for medical laser delivery system which provides high power transmission capability for infrared light while maintaining the flexibility associated with conventional fiber delivery systems.

SUMMARY OF THE INVENTION

The present invention comprises a medical laser apparatus that delivers infrared laser light to a treatment site through an optical waveguide. The waveguide comprises a guiding structure surrounded by a protective structure. The guiding structure comprises a fluoride-based material, examples of which are zirconium fluoride, aluminum fluoride, and hafnium fluoride. The guiding structure is capable of transmitting infrared light preferably having a wavelength of about three microns at a power density of at least 4 kilowatts per square centimeter. The guiding structure preferably comprises an inner core and an outer cladding which has a lower index of refraction than the inner core. In one embodiment, the guiding structure comprises a multi-mode, step-index optical fiber, having a single core and a single cladding. Alternatively, the guiding structure can comprise a double clad multimode-fiber which consists of a core, an inner cladding and an outer cladding. In either case, the multi-mode fiber preferably transmits light from an Er:YAG laser at a wavelength of about three microns and light from a Nd:YAG laser at a wavelength of about one micron simultaneously through the optical fiber.

The protective structure is substantially moisture resistant, and is disposed to receive a portion of the energy travelling through the guiding structure which escapes through leaky modes of the guiding structure. The protective structure is also flexible, but has a high enough resistance to bending to protect the guiding structure from breakage. Additionally, the protective structure has a sufficiently high transmittance to infrared light in the wavelengths mentioned above to allow the energy escaping from the guiding structure to be dissipated without damaging the guiding structure. In the preferred embodiment, the protective structure, which is polyimide, consists only of polyimide.

In various other embodiments of the invention, the protective structure possesses such desirable properties as having a glass transition temperature $T_g$ of at least 340° C., having a tensile strength of at least about 19,000 psi, and having a thermal conductivity of at least about $35 \times 10^{-5}$ cal/(cm)(sec)(°C.). Preferably, the protective structure is sufficiently transmissive such that it absorbs no more than 10–20% of the energy which escapes the guiding structure in the form of leaky modes, and it is preferably bonded to the guiding structure. In one embodiment, the protective structure has a higher refractive index than the cladding of the guiding structure.

One aspect of the present invention is that an infrared laser, such as an Er:YAG laser with an output wavelength of 2.94 μm, is used to supply laser energy to the guiding structure. The laser produces a beam of infrared laser light which is incident on the end of the core. The beam has an energy profile which is substantially entirely within the numerical aperture of the guiding structure. The incident beam produces a spot on the end of the core of the guiding structure, the size of which is such that all of the energy within the $1/e^2$ radius of the beam is within 80% of the core diameter. The laser beam preferably consists essentially of light in the $TE_{00}$ mode.

Another aspect of the present invention is that an input end portion of the guiding structure is stripped off its protective structure, and a rigid tubular sleeve made of a highly infrared transmissive material such as IR grade fused silica is placed over this end portion. The guiding structure fits into the sleeve such that it is in contact with the sleeve's inner wall. There is preferably no intervening material between the cladding and the inner wall of the sleeve (other than a few micron thickness of air).

BRIEF DESCRIPTION OF THE DRAWINGS

FIG. 1 is a diagram of a laser delivery apparatus in accordance with the present invention.

FIG. 1A is an enlarged view in partial cross section of the laser coupling assembly of FIG. 1.

FIG. 2 is a cross-sectional view of an optical waveguide in accordance with the present invention, surrounded by a protective jacket.

FIG. 3 is a cross-sectional view of an alternate embodiment of the optical waveguide, surrounded by a protective jacket.

DETAILED DESCRIPTION OF THE PREFERRED EMBODIMENT

Figure 4:
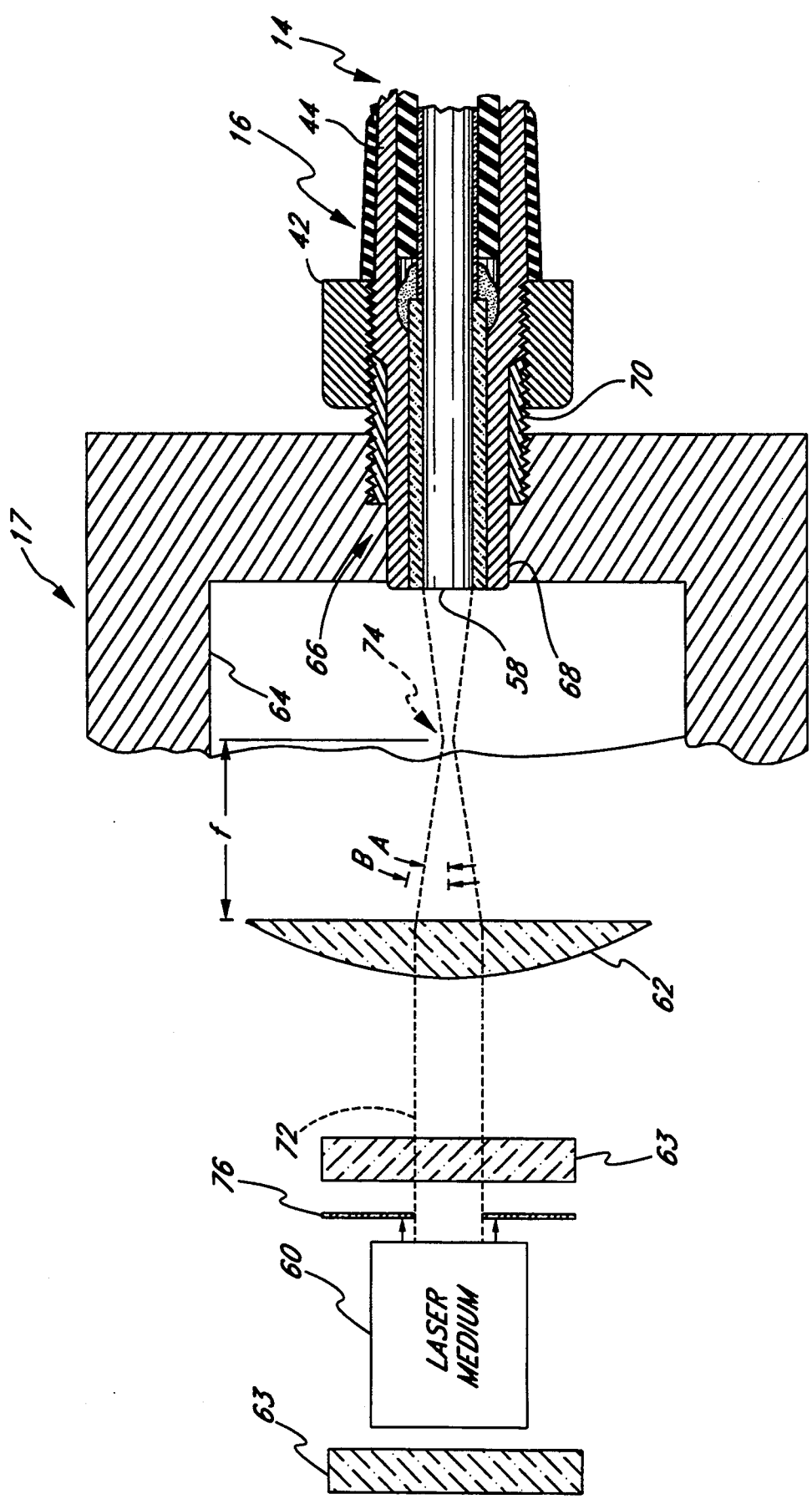
FIG. 4 is a diagram of a laser coupled to the coupling assembly of FIG. 1A.

As shown in FIGS. 1 and 2, the present invention comprises a medical laser delivery system 10 comprising a handpiece 12, an optical waveguide 14 and an input coupling assembly 16 for attaching the waveguide 14 to a laser 17 (shown in FIG. 4). The handpiece 12 has larger diameter than the waveguide 14 and is shaped so that it is easily manipulated by the hand of a user. The hand piece 12 may possess ridges 18 on its exterior to secure a person's grip on the handpiece 12. The handpiece 12 comprises a body portion 20, sized for grasping by the hand of a user, and a guide portion 22 which projects distally therefrom. The guide portion 22 comprises a stainless steel tube through which a distal portion 24 of the waveguide 14 extends, and the guide portion 22 functions to provide rigidity to the distal end 24 of the waveguide 14. If desired, the distal end of the guide portion 22 may be threaded so as to allow different tips to be attached to the handpiece 12. Such tips may be used to generate various beam profiles for the output laser beam (e.g., by means of lenses or other optical elements), and their use is well known in the art.

A cross-sectional view of the optical waveguide 14 is illustrated in FIG. 2. The overall length of the waveguide 14 of the preferred embodiment is about one meter. The waveguide 14 comprises a guiding structure 25 surrounded by a protective structure 26. Optionally, the protective structure 26 may be covered by an outer flexible sleeve or jacket 27. The guiding structure 25 comprises a multimode optical fiber having an inner core 28 and an outer cladding 30. The core 28 and cladding 30 are made of a fluoride-based material such a zirconium fluoride, aluminum fluoride, or hafnium fluoride. The core 28 and cladding 30 are fluoride doped with impurities such that the cladding 30 has a lower index of refraction than the core 28. In one embodiment, the refractive index of the core 28 is 1,511 and the refractive index of the cladding 30 is 1.497. The guiding structure is manufactured using conventional optical fiber manufacturing techniques which are well known in the art.

In the preferred embodiment, the protective structure 26 comprises a buffer material which is highly transmissive to infrared light, sufficiently strong to protect the fiber against breakage, flexible and moisture resistant. The preferred buffer material comprises a layer of thermoplastic polyimide having a thickness of 0.01 mm (such as Pyralin TM, available from DuPont). The polyimide comprises linear polymers having generally the imide group—CONCO— as part of the polymer chain. The polyimide buffer material surrounds and is bonded to the cladding 30 using conventional techniques. Polyimide has a glass transition temperature of about 340° C., a tensile strength of about 19,000 psi, a thermal conductivity of about 0.00035 cal/(cm)(sec)(°C.), and an index of refraction of about 1.7 (e.g., 1,623). It has been found that, when used as a buffer for a fluoride-based fiber, polyimide dramatically increases the power handling capability of the fiber such that sustained transmission of infrared light having a wavelength of about 3 microns is possible at a power density of at least 4 kW/cm² over a fiber length of about 1 to 3 meters. Accordingly, the present invention permits fiber optic delivery of the high intensity levels required for aggressive cutting of hard tissue such as bone. In effect, the polyimide dissipates the energy from leaky modes of the fiber without creating hot spots which could damage the fiber.

The outer jacket 28, if used, may comprise either PVC or polysulfone tubing. The jacket 28 is sized to fit over the protective structure 26 and slides thereon without being bonded thereto.

A cross-sectional view of an alternative embodiment of the optical waveguide 14 is illustrated in FIG. 3. The alternative embodiment comprises a double clad fiber 34 which comprises the core 28, surrounded by an inner cladding 36, which in turn is surrounded by an outer cladding 38. The double clad fiber 34 is surrounded by the protective structure 26 and the jacket 28 of the preferred embodiment of the optical waveguide 14. The protective structure 26 of the preferred embodiment comprises a layer of polyimide material, as described above, that has an index of refraction, higher than that of the claddings 36, 38. The outer cladding 36 is provided to inhibit light propagating in leaky modes of the inner cladding 38 from reaching the polyimide protective structure 26, and the outer cladding has a lower index of refraction than the inner cladding 36 for this purpose. Most of the light in the inner cladding 36 will thus be guided within the inner cladding 36 due to the fact that the index of refraction for the inner cladding 36 is higher than that of the outer cladding 38. Accordingly, by adding an extra layer of cladding, light leaking out of the core 28 is advantageously kept within the inner cladding area to decrease the amount of energy reaching the protective structure through leaky modes.

Referring back to FIG. 1, the optical waveguide 14 extends through the center of the handpiece 12 and emerges at the distal end 24, creating a path for laser light to travel through the handpiece 12 and out the distal end 24 to the tissue site T. The waveguide 14 is protected from breakage at the point of entry to the handpiece 12 by a strain relief 40. The strain relief is preferably made of PVC tubing.

A cross-sectional view of the input coupling assembly 16 is shown in FIG. 1A. The coupling assembly 16 comprises a lock nut 42, a male fitting 44, a tubular sleeve 46 of IR grade silica and a strain relief 47. Both the male fitting 44 and the lock nut 42 are made of stainless steel (i.e., an SMA-905 connector). The male fitting 44 comprises a narrow tubular proximal end portion 48 which has a smaller diameter than a tubular distal portion 50. The exterior of the wider distal portion 50 is partially threaded so that the lock nut 42 may be screwed over it. The inner diameter of the distal portion 50 of the fitting is approximately equal to the diameter of the waveguide 14 (including any outer jacket 28).

The sleeve 46 is located within the inner diameter of the narrow proximal end 48 of the male fitting 44, and has a wall thickness which may be about 300% of the cladding thickness. The outer diameter of the sleeve 46 is equal to the inner diameter of the fitting 44 in the proximal end portion 48. However, in the wide portion 50, the inner diameter of the fitting 44 becomes larger, leaving a recess 52 between the tubing 46 and the inner wall of the fitting 44. A proximal end portion of the waveguide 14 is inserted into the sleeve 46. This portion has the jacket 28 (FIG. 2) and the polyimide buffer 26 removed, leaving only the guiding structure 25. The buffer 26 terminates at the inner end of the sleeve 46. The guiding structure 25 is inserted within the sleeve 46, and the sleeve 46 is sized so that the guiding structure 25 is flush against the inner wall of the quartz sleeve 46 without intervening material such that it is not bonded to the sleeve 46. The waveguide 14 is fastened to the sleeve 46 by epoxy glue 54 which is placed in the recess 42 between the inner wall of the fitting 44 and the waveguide 14. A proximal end 58 of the waveguide 14 is cleaved or dry-polished with the sleeve 46 mounted thereon so that the input face formed by the sleeve and guiding structure is sufficiently smooth to prevent significant scattering of light as it enters the waveguide. The polishing is accomplished using 9 micron, 5 micron and 0.3 micron polishing paper. Preferably, the polishing is accomplished "dry," without water or by oil base polishing, since fluoride-based fibers have an affinity for water and light from an Er:YAG laser is strongly absorbed by water.

FIG. 4 illustrates the attachment of the coupling assembly 16 of the waveguide 14 to the laser 17. The laser 17 comprises an infrared lasing medium 60 (e.g. a solid rod of Er:YAG) disposed between a rear reflector 61 and a front output coupler 63. The reflector 61 reflects 99.5% of the light incident thereon while the output coupler 63 reflects about 90% of the light incident thereon to form a laser cavity. A focusing lens 62 focuses light from the laser cavity for input to the coupling assembly 16. The preferred embodiment uses an Er:YAG laser and a plano-convex lens, but other arrangements may be used. The laser medium 60 and the lens 62 are contained within a chassis 64. The chassis 64 has a female fitting 66 comprising a hole 68 having a slightly larger diameter than the narrow end 48 of the male fitting 44 to enable insertion of the narrow end 48 into the hole 68, and a threaded sleeve 70 having an inner diameter slightly larger than that of the hole 68, and an outer diameter sized to receive the lock nut 42 (FIG. 1A). The narrow end 48 of the male fitting 44 is inserted into the hole 68, and the lock nut 42 is screwed onto the sleeve 70, thereby securing the male fitting 44 to the chassis 64. The axial length of the sleeve 70 and thickness of the chassis 64 are such that the proximal end 58 of the waveguide 14 projects slightly past the interior surface of the chassis 64.

The laser cavity emits a laser beam 72 which propagates through the lens 62 and is focused at a focal point 74. The end 58 of the optical waveguide 14 is located just past the focal length f of the lens. The focusing of the laser beam 72 will produce a small beam spot on the end 58 of the waveguide 14. It is desirable that the laser beam's spot diameter be incident within 80% of core 28 to minimize the amount of the laser light incident on the sleeve 46 of the coupling 16. The positioning of the waveguide 14 in relation to the focal length f of the lens is important to insure that the laser beam's spot be incident within 80% of the core 28, as the spherical aberration of the focused spot is larger than the actual laser's focused spot diameter. As is well known, the diameter of the beam spot at the focal point 74 is a function of the focal length f of the lens 62 and the divergence angle of the laser beam 72. One embodiment of the invention uses a lens with a 15 mm focal length f. The energy distribution within the spot is a function of the modes of the laser cavity. The $TE_{00}$ mode of the laser cavity is the lowest order mode. It has an intensity distribution which follows a gaussian curve so that the peak energy is located at the center of the beam. The $TE_{00}$ mode is therefore desirable because it produces maximum intensity at the center of the beam spot. In order to limit the output of the multimode laser cavity to the $TEM_{00}$ mode, a restricting aperture 76 is placed in the path of the beam 72 inside the laser cavity between the laser medium 60 and the output coupler 63.

It is also desirable to keep the focused optical energy within the numerical aperture of the guiding structure 25. The numerical aperture (N.A.) of the guiding structure for the $TE_{00}$ mode is the sine of the maximum acceptance half angle within which light entering the core 28 will undergo total internal reflection and therefore remain within the core 28. The N.A. of the fiber is found by the equation:

$$N.A. = \sqrt{n_1^2 - n_2^2}$$

where $n_1$ is the refractive index of the core 28 and $n_2$ is the refractive index of the cladding 30. The N.A. of the laser beam 72 entering the core 28 is equal to the beam diameter before entering the lens 62 divided by twice the focal length of the lens. To reduce losses and heat damage, it is preferable that the numerical aperture of the waveguide 14 be greater than the numerical aperture of the beam 72; or stated another way, that the convergence angle A of the beam 72 be less than the acceptance angle B of the waveguide 14. The restricting aperture 76 additionally serves to reduce beam divergence and to keep the beam diameter within the limits needed to produce a numerical aperture within that of the guiding structure 25.

During operation, the multimode laser beam 72 is restricted by the aperture 76 to produce the $TE_{00}$ mode, and focused by the lens 62 onto the end 58 of the fiber core 28 (FIG. 2). The light travels through the waveguide 14 to the distal end 24 where it may be further focused by a lens 62 or directly transmitted to the tissue site. The physician performing a surgical operation holds the handpiece 12 to direct the laser beam 72 to any desired target location T. The preferred application of the present invention is laser surgery, particularly the cutting of tissue, including hard tissue such as bone. In this regard, the waveguide 14 must be capable of transmitting light having high power densities, at least 4 kilowatts per square centimeter at a wavelength of about 3.0 microns (2.94 for Er:YAG). Preferably, the laser 17 is pulsed at a repetition rate of 1 to 30 pulses per second, with a pulse duration of 250 μsec to 300 μsec, and a pulse energy of 5 to 300 mJ per pulse. In the preferred embodiment, each pulse is comprised of a train or burst of sub-pulses, each having a duration of about 200 nsec.

Figure 5:
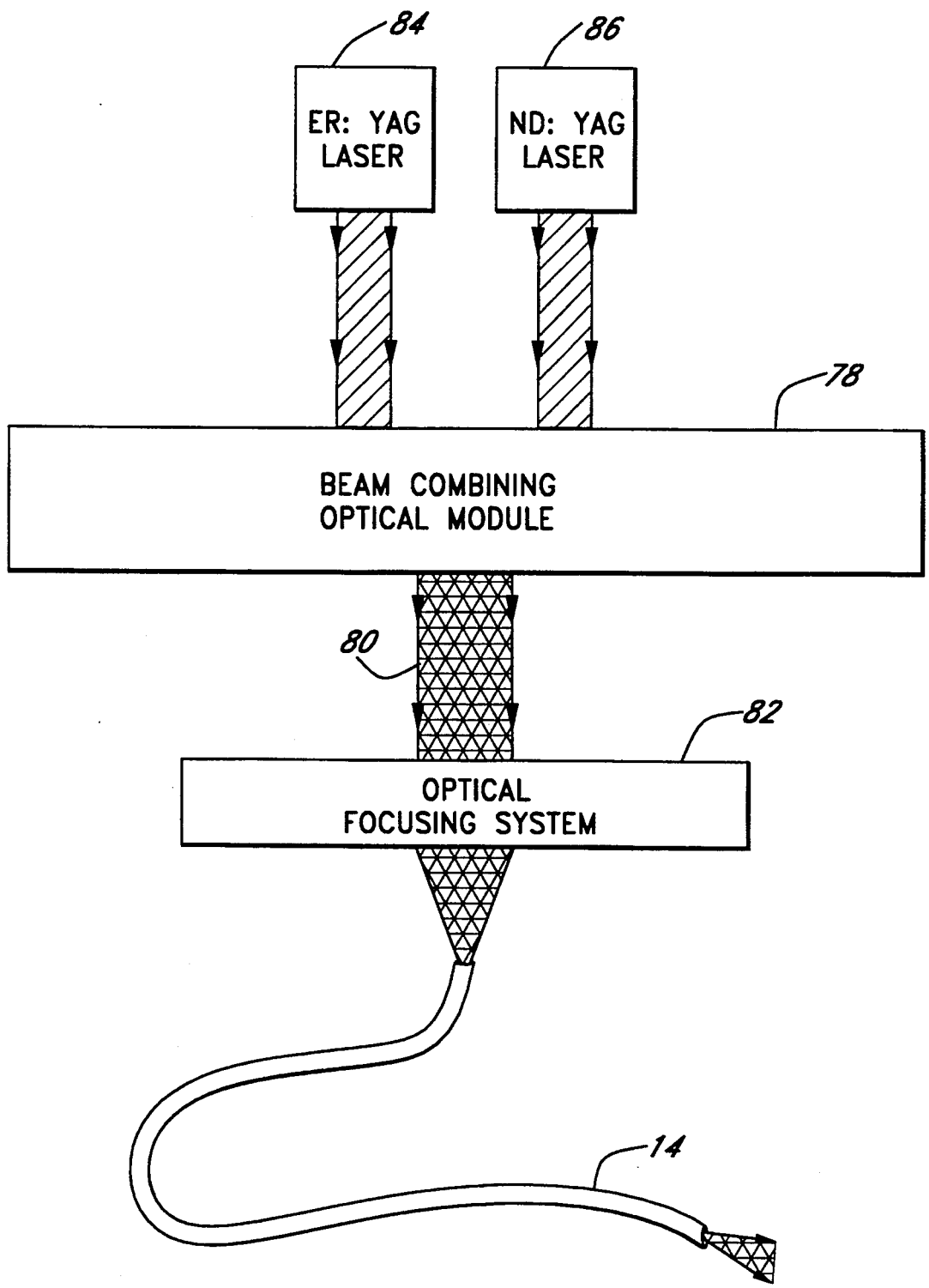
FIG. 5 is a diagram of a laser delivery system for producing multi-wavelength light input into a multi-mode laser delivery device of an alternate embodiment of the present invention.

In an alternate embodiment illustrated in FIG. 5, light from multiple lasers is combined by a beam combining module 78 to generate a combined beam 80 of multiple wavelengths of laser light. The combined beam 80 is focused into the waveguide 14 using an optical focusing system 82, for propagation through the waveguide 14 of the present invention. Two preferred lasers used in the multi-wavelength alternate embodiment of the fiber are a pulsed cutting laser 84, with a wavelength of about 3.0 microns (preferably 2.94 microns for Er:YAG) and a continuous wave coagulating laser 86, with a wavelength of about 1 micron (preferably 1.06 microns for Nd:YAG). However, in general, the wavelengths used for cutting may be from 0.193 microns to 308 microns and 2.1 microns to 10.6 microns, while the wavelengths used for coagulation may be from 0.532 microns to 2.1 microns. The combination of a coagulating laser such as the Nd:YAG laser 86 with a precise hard tissue cutting laser such as the Er:YAG laser 84 is advantageous for surgery in almost every medical specialty, but particularly in neurosurgery and general surgery. The combination of these two wavelengths in the same fiber enables the simultaneous application of the lasers to cut and coagulate precisely the same location at the same time.

The preferred embodiment of the optical waveguide 14 is especially advantageous for simultaneous delivery of multiple wavelength lasers. Two waves of different frequencies have a tendency to interact during propagation through a multi-mode waveguide which cause localized variations in the energy levels, thereby causing energy concentrations and increased energy propagation into leaky modes. As mentioned above, the preferred embodiment of the waveguide 14 uses a polyimide protective structure, which enables the variations caused by the combination of the Er:YAG laser 84 and the Nd:YAG laser 86 to dissipate without damaging the waveguide 14.

The waveguide 14 preferably transmits a combined beam of two infrared wavelengths (e.g. 1.06 microns and 2.94 microns) to a treatment site for laser surgery. In this regard, the waveguide 14 must transmit light having high power densities, at least 4 kilowatts per square centimeter at combined wavelength of about 3.0 microns (2.94 for Er:YAG) and 1.0 microns (1.06 for Nd:YAG). Preferably, the pulsed cutting laser 84 laser is pulsed at a repetition rate of 1 to 30 pulses/sec, a pulse train duration of 200 μsec to 450 μsec, and a pulse energy of 5 to 300 mJ per pulse while the coagulating laser 86 delivers a continuous beam of power of 15-25 watts. Although simultaneous transmission of the two wavelengths is preferred, the wavelengths may also be transmitted alternately by selectively energizing the laser sources 84, 86.

What is claimed is:

1. A medical laser apparatus for delivering infrared energy to a treatment site, said apparatus comprising a waveguide, said waveguide comprising:

a guiding structure which transmits invisible infrared light at a wavelength of about 3 microns at a power density of at least about 4 kilowatts per square centimeter, said guiding structure consisting of a core having a refractive index and at least one cladding having a refractive index lower than that of said core, said core being comprised of a compound that includes a metal; and a protective structure comprising a material which is substantially impermeable to moisture and has a moisture resistance significantly higher than that of said guiding structure, said protective structure surrounding said guiding structure and juxtaposed therewith such that said protective structure receives a portion of said infrared light having said power density, said portion of said light received by said protective structure being in the form of leaky modes, said protective structure being flexible and having relatively high resistance to bending compared to said guiding structure to protect said guiding structure against breakage, said protective structure additionally having a sufficiently high transmittance to said infrared light, such that the energy of said light in said leaky modes is dissipated from said protective structure without damaging said waveguide; and said apparatus additionally comprising a source of infrared light coupled to said waveguide to produce a power density of at least 4 kilowatts per square centimeter in said core.

2. The apparatus of claim 1, wherein at least one cladding comprises an inner cladding having a refractive index lower than that of said core and an outer cladding having a refractive index lower than that of said inner cladding.

3. The apparatus of claim 2, wherein said guiding structure comprises a multi-mode optical fiber.

4. The apparatus of claim 1, wherein said protective structure comprises a jacket comprised of polyimide.

5. The apparatus of claim 1, wherein said guiding structure comprises hafnium fluoride.

6. The apparatus of claim 1, wherein said guiding structure comprises zirconium fluoride.

7. The apparatus of claim 1, wherein said protective structure has a glass transition temperature of at least about 340° C.

8. The apparatus of claim 1, wherein said transmittance of said protective structure is such that no more than about 10–20% of the energy in said leaky modes is absorbed by said protective structure.

9. The apparatus of claim 1, wherein said protective structure comprises a material having a tensile strength of at least about 19,000 psi.

10. The apparatus of claim 1, wherein said protective structure is comprised of a material having a thermal conductivity of at least about $35 \times 10^{-5}$ cal/(cm)(sec)(°C.)

11. The apparatus of claim 1, wherein said guiding structure comprises a multi-mode optical fiber.

12. The apparatus of claim 1, wherein said protective structure has a higher refractive index than said cladding.

13. The apparatus of claim 1 wherein said source of light comprises a medical laser which produces a beam of said infrared light, said beam being directed so that the energy of said beam is incident on an end of said core with substantially all of said beam within the numerical aperture of said guiding structure, said beam having a spot size such that substantially all of the energy within the $1e^2$ radius of said beam is incident on the core of said guiding structure.

14. The apparatus of claim 13, wherein said medical laser comprises an Er:YAG laser.

15. The apparatus of claim 1, wherein said beam of infrared light consists essentially of light in a $TEM_{00}$ mode.

16. The apparatus of claim 15, wherein said protective structure terminates at a location spaced from said end of said guiding structure, said end of said guiding structure being surrounding by a sleeve which is transmissive to said infrared light.

17. The apparatus of claim 16, wherein said sleeve comprises infrared grade fused silica.

18. The apparatus of claim 17, wherein said sleeve is disposed around said end of said guiding structure such that said sleeve is in direct contact with said waveguide, without intervening material therebetween.

19. The apparatus of claim 1, wherein said source of infrared light produces light having a wavelength of 2.94 microns.

20. The apparatus of claim 1, wherein said protective structure is bonded to the cladding of said guiding structure.

21. A medical laser apparatus comprising:
a fluoride-based optical fiber having a core and a cladding;
an erbium YAG laser coupled to said optical fiber, said erbium YAG laser producing invisible infrared light at a wavelength of about 3 microns, said infrared light propagating in said core at a power density of at least 4 kilowatts per square centimeter; and
a polyimide buffer surrounding said optical fiber.

22. The apparatus of claim 21, wherein the polyimide buffer comprises linear polymers.

23. A medical laser apparatus for delivering multiple wavelengths of optical energy to a treatment site, comprising:
a waveguide comprising a fluoride-based guiding structure which transmits invisible infrared light at a first wavelength efficacious for cutting tissue and light at a second wavelength efficacious for coagulating tissue, said guiding structure transmitting light at a power density of at least about 4 kilowatts per square centimeter, said guiding structure consisting of a core having a refractive index and at least one cladding having a refractive index lower than that of said core, said wave guide additionally comprising a protective structure comprising a material which is substantially impermeable to moisture and has a moisture resistance significantly higher than that of said guiding structure, said protective structure surrounding said guiding structure and juxtaposed therewith such that said protective structure receives a portion of said light having said power density, said portion of said light received by said protective structure being in the form of leaky modes, said protective structure being flexible and having relatively high resistance to bending compared to said guiding structure to protect said guiding structure against breakage, said protective structure additionally having a sufficiently high transmittance to said light, such that the energy of said light in said leaky modes is dissipated from said protective structure without damaging said waveguide;
a first laser, coupled to said waveguide, for providing light at said first wavelength at a dosage sufficient to cut tissue; and
a second laser, coupled to said waveguide, for providing light at said second wavelength at a dosage sufficient to coagulate tissue.

24. The apparatus of claim 23, wherein said guiding structure comprises a multi-mode optical fiber.

25. The apparatus of claim 23, wherein said first wavelength is 2.94 microns and said second wavelength is 1.06 microns.

26. The apparatus of claim 23, wherein said first laser comprises an Er:YAG laser and said second laser comprises a Nd:YAG laser.

27. The apparatus of claim 23, wherein at least one cladding comprises an inner cladding having a refractive index lower than that of said core and an outer cladding having a refractive index lower than that of said inner cladding.

28. The apparatus of claim 27, wherein said guiding structure comprises a multi-mode optical fiber.

* * * * *

UNITED STATES PATENT AND TRADEMARK OFFICE
CERTIFICATE OF CORRECTION

PATENT NO. : 5,349,590
DATED : September 20, 1994
INVENTOR(S) : Varouj D. Amirkhanian, et. al.

It is certified that error appears in the above-identified patent and that said Letters Patent is hereby corrected as shown below:

Column 9, line 21, change "$1e^2$ radius" to --$1/e^2$ radius--
Column 9, line 31, change "being surrounding" to --beingsurrounded--.

Signed and Sealed this

Tenth Day of March, 1998

BRUCE LEHMAN

*Attest:*

*Attesting Officer*        Commissioner of Patents and Trademarks